US00PP08841P

United States Patent [19]

Meilland

[11] Patent Number: Plant 8,841

[45] Date of Patent: Jul. 19, 1994

[54] ROSE PLANT—MEIPOTAL VARIETY

[75] Inventor: Alain A. Meilland, Antibes, France

[73] Assignee: The Conard-Pyle Company, West Grove, Pa.

[21] Appl. No.: 119,373

[22] Filed: Sep. 10, 1993

[51] Int. Cl.[5] ..... A01H 5/00
[52] U.S. Cl. ..... Plt./1
[58] Field of Search ..... Plt. 1, 22

*Primary Examiner*—Howard J. Locker
*Attorney, Agent, or Firm*—Burns, Doane, Swecker & Mathis

[57] ABSTRACT

A new and distinct variety of shrub rose plant is provided which forms continuously throughout the season attractive simple marbled Carmine Rose blossoms. The blossoms commonly are formed very abundantly and continuously and possess firm petals which detach cleanly. The vegetation is vigorous and the plant possesses a bushy growth habit. The new variety is not particularly affected by cryptogamic diseases, it exhibits excellent winter hardiness, it possesses decorative glossy foliage, and it is well suited for use as ornamentation in the landscape.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female (i.e., the seed parent) was the product of the pollination of the Maceye variety (U.S. Plant Pat. No. 3,985) and the Meirisouru variety (non-patented in the United States). The Maceye variety sometimes is known as the Eye Paint variety and the Meirisouru variety sometimes is known as the Nirvana variety. The male parent (i.e., the pollen parent) of the new variety was the Intersmat variety (non-patented in the United States. The parentage of the new variety can be summarized as follows:

(MACEYE×MEIRISOURU×INTERSMAT.

The seeds resulting from the above pollination were sown and 71 small plants were obtained which were physically and biologically different from each other. Selective study resulted in the identification of a single plant of the new variety.

It is found that the new variety of shrub rose plant possesses the following combination of characteristics:

(a) forms continuously throughout the season attractive simple blossoms which are marbled Carmine Rose in coloration,
(b) forms blossom petals which are firm and drop off cleanly,
(c) forms attractive glossy foliage,
(d) exhibits a bushy growth habit,
(e) forms light green adult wood,
(f) exhibits excellent disease resistance,
(g) exhibits excellent winter hardiness, and
(h) is particularly well suited for growing in the landscape.

The new variety meets the needs of the horticultural industry for many uses. It can be grown to particular advantage as attractive ornamentation in parks, gardens, public areas, and residential landscapes.

The characteristics of the new variety have been found to be homogeneous and stable and are strictly transmissible by asexual propagation carried out in France (e.g., by budding, grafting, cuttage, etc.) from one generation to another.

The new variety has been named the Meipotal variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years of age and were grown on their own roots in the open air at Le-Cannet-des-Maures, Var, France.

FIG. 1—illustrates a specimen of a young shoot;

FIG. 2—illustrates a specimen of floral buds before the opening of the sepals;

FIG. 3—illustrates a specimen of floral buds as the sepals open;

FIG. 4—illustrates a specimen of floral buds as the petals open;

FIG. 5—illustrates a specimen of a flower in the course of blooming;

FIG. 6—illustrates a specimen of a open flower - plan view - obverse;

FIG. 7—illustrates a specimen of an open flower - plan view - reverse;

FIG. 8—illustrates a specimen of an open flower immediately prior to petal drop - plan view - obverse;

FIG. 9—illustrates a specimen of a open flower immediately prior to petal drop - plan view - reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of leaves with three leaflets - upper and under surfaces;

FIG. 15—illustrates a specimen of leaves with five leaflets - upper and under surface; and FIG. 16—illustrates a specimen of leaves with seven leaflets - plan view - upper and under surfaces.

DETAILED DESCRIPTION

Figures 1, 2, 3, 4, 5, 6, 7, 8, 9, 10, 11, 12, 13, 14, 15, 16:
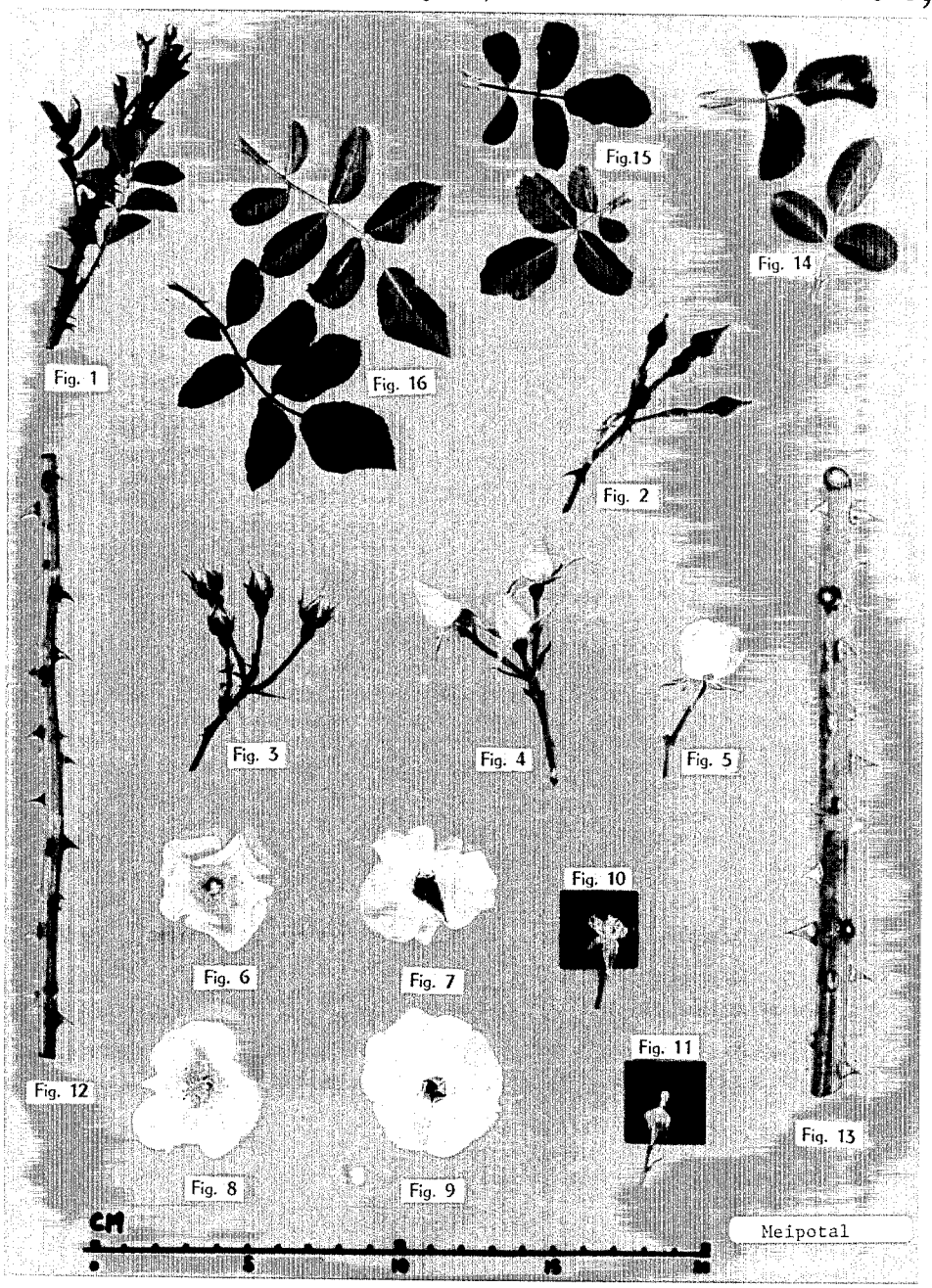

The chart used in the identification of the colors is that of The Royal Horticultural Society (R.H.S. Colour Chart). The terminology preceding the numbered reference has been added to indicate in common terms the corresponding color. The description is based on the observation of two year old specimens of the new variety while grown outdoors on their own roots at Le-Cannet-des-Maures, Var, France.

Class: Shrub.

Plant:

*Height.*—Approximately 70 to 80 cm. on average when fully mature after two growing seasons on own roots.

*Habit.*—Bushy.

Branches:

*Color.*—Young stems: medium green, Green Group 143A. Adult wood: light green, Green Group 143C.

Leaves:

*Stipules.*—Adnate, pectinate, and linear.

*Petioles.*—Upper surface: striped reddish brown on young foliage and green medium green on adult foliage with glandular edges. Under surface: light green with a few prickles.

*Leaflets.*—Number: 3, 5 (most often), and 7. Shape: oval to round. Serration: single and regular. Texture: rough. General appearance: dense glossy foliage. Color (young foliage): Upper surface: dark lettuce green, Yellow-Green Group 144A, with reddish edges. Under surface: light green, Yellow-Green Group 146C, slightly suffused with a reddish tint. Color (adult foliage): Upper surface: deep green, Green Group 137A. Under surface: light green, Green Group 137D.

Inflorescence:

*Number of flowers.*—Approximately 1 to 10 flowers per stem.

*Peduncle.*—Medium green, more or less shaded with reddish-brown coloration and with some pediculate glands, approxiamtely 2 to 3 cm. in length on average.

*Sepals.*—Upper surface: tomentose, greenish in coloration with a more or less brownish tint. Under surface: medium green with a more or less reddish tint and with appendiculated edges.

*Buds.*—Shape: conical. Length: approximately 1.5 cm. on average. Size: small. Color when opening: Upper surface: pale Chinese Yellow, Yellow-Orange Group 20D, and broadly suffused with light Blood Red, Red Group 45D, with a white eye. Under surface: on the outside of the petal, Blood Red, Red Group 45A, and broadly dotted with light Turkey Red, Red Group 46D; and on the inside of the petal, pale Chinese Yellow, Yellow-Orange Group 20D.

*Flower.*—Form: simple, opens as a flat cup. Diameter: approximately 5 to 5.5 cm. on average. Color (when opening begins): Upper surface: pale Chinese Yellow, Yellow-Orange Group 20D, suffused and/or marbled with light Blood Red, Red Group 45D, with a white eye. Under surface: on the outside of the petal, Carmine Rose, Red Group 52B, suffused with Crimson, Red Group 52A; and on the inside of the petal, pale Chinese Yellow, Yellow-Orange Group 20D, tinted with light Blood Red, Red Group 45D. Color (when blooming): Upper surface: Carmine Rose, Red Group 52B, marbled with white at the circumference of the petals. Under surface: pale Orient Pink, Red Group 36D, more or less suffused with Carmine Rose, Red Group 52D. Color (at end of opening): Upper surface: Carmine Rose, Red Group 52D, marbled with white at the circumference of the petals. Under surface: pale Orient Pink, Red Group 36D, more or less suffused with Carmine Rose, Red Group 52D. Fragrance: slight. Lasting quality: long. Petal shape: flat with more or less indented tips and a slight undulation. Texture: firm. Petal member: approximately 5 on average. Petal drop: very good. Stamen number: approximately 103 on average. Anthers: bright yellow in coloration. Filaments: bright yellow and somewhat evenly positioned on the receptacle circumference. Pistils: approximately 25 on average. Stigmas: greenish-yellow and of approximately the same height as the stamens. Styles: more or less twisted, greenish in coloration, and sometimes fused together. Receptacle: medium green and reddish tinted at the dehiscence of the anthers and in longitudinal section it is narrow and pear-shaped.

Development:

*Vegetation.*—Strong, vigorous.

*Blooming.*—Very abundant and continuous.

*Aptitude-to bear fruits.*—Good.

*Resistance to frost.*—Excellent.

*Resistance to diseases.*—Very good.

I claim:

1. A new and distinct variety of shrub rose plant characterized by the following combination of characteristics:

(a) forms continuously throughout the season attractive simple blossoms which are marbled Carmine Rose in coloration,
(b) forms blossom petals which are firm and drop off cleanly,
(c) forms attractive glossy foliage,
(d) exhibits a bushy growth habit,
(e) forms light green adult wood,
(f) exhibits excellent disease resistance,
(g) exhibits excellent winter hardiness, and
(h) is particularly well-suited for growing in the landscape;

substantially as herein shown and described.

* * * * *

CM
Meipotal